(12) United States Patent
Klausmeyer

(10) Patent No.: US 6,534,688 B2
(45) Date of Patent: Mar. 18, 2003

(54) DEHYDROCHLORINATION STABILIZATION OF POLYCHLORINATED ALKANES

(75) Inventor: Rodney L. Klausmeyer, Wichita, KS (US)

(73) Assignee: Vulcan Chemicals, Birmingham, AL (US)

( * ) Notice: Subject to any disclaimer, the term of this patent is extended or adjusted under 35 U.S.C. 154(b) by 0 days.

(21) Appl. No.: 09/877,201

(22) Filed: Jun. 11, 2001

(65) Prior Publication Data

US 2003/0018225 A1 Jan. 23, 2003

(51) Int. Cl.$^7$ .............................................. C07C 17/42
(52) U.S. Cl. .................................... 570/264; 570/262
(58) Field of Search .................................. 570/264, 262

(56) References Cited

U.S. PATENT DOCUMENTS

| | | |
|---|---|---|
| 3,346,651 A | 10/1967 | Moakes |
| 3,696,050 A | 10/1972 | Werts et al. |
| 4,307,261 A | 12/1981 | Beard, Jr. et al. |
| 4,412,086 A | 10/1983 | Bear, Jr. et al. |
| 4,535,194 A | 8/1985 | Woodard |
| 4,542,231 A | 9/1985 | Dougherty et al. |
| 4,605,802 A | 8/1986 | Astrologes |
| 4,803,009 A | 2/1989 | Gorski |
| 4,804,493 A | 2/1989 | Gorski |
| 4,961,870 A | 10/1990 | Cook et al. |
| 5,569,794 A | 10/1996 | Tung |
| 5,683,554 A | 11/1997 | Brooks et al. |
| 5,902,914 A | 5/1999 | Rygas et al. |
| 6,187,978 B1 | 2/2001 | Rygas et al. |

FOREIGN PATENT DOCUMENTS

| | | |
|---|---|---|
| DE | 1243172 | 6/1967 |
| DE | 2008617 | 10/1970 |
| DE | 2148185 | 4/1973 |
| EP | 371821 A1 | 6/1990 |
| FR | 2297213 | 8/1976 |
| GB | 1265567 A1 B | 3/1972 |
| JP | 46005289 B4 | 12/1971 |
| JP | 47011045 B4 | 4/1972 |
| JP | 48092310 | 11/1973 |
| JP | 50088007 | 7/1975 |
| JP | 06025027 A2 | 2/1994 |
| JP | 09183742 A2 | 7/1997 |
| NL | 6602762 | 9/1966 |
| NL | 6609828 | 1/1967 |

OTHER PUBLICATIONS

CA 118:234530; Grishin, A. N.; Zegelman, V. I.; Fomin, V. A.; Etlis, I. V.; Popov, V. A.; Khavritsyn, A. A., "Process controlling of vinyl chloride polymerization in mass (suspension) with high degree of conversion"; Res. Inst. Polym. Chem. Technol., Dzerzhinsk, Russia Dechema monogr., 127 (Int. Workshop Polym. React. Eng., 4th, 1992, 449–459 (English) 1992.

CA 109:151482; Sherman, A. M.; "Balancing formulation storage stability and cure behavior through the use of photoinitiator blends"; Radcure '86, Conf. Proc., 10th, 4/13–4/25, Assoc. Finish. Processes SME:Dearborn, Mich. (English) 1986.

CA 102:181864; Klopman, G.; Namboodiri, K.; Schochet, M.; "Simple method of computing the partition coefficient"; J. Comput. Chem., 6(1), 23–38 (English) 1985.

CA 99:123046; Kolesnikov, V. Y; Popov, V. A.; Zvereva, Y. A.; Zegel'Man, V. I., Shvarev, E. P.; "Kinetic methods for the control of vinyl chloride polymerization"; Plast. Massy (8), 7–8 (Russian) 1983.

CA 83:193849; Gladyshev, G. P.; Zvereva, Y. A.; Popov, V. A.; Shvarev, E. P.; Pen'Kov, E. I.; "Control of vinyl chloride polymerization rate using weak initiators"; Plast. Massy (9), 73 (Russian) 1975.

CA83:98026; Popov, V. A.; Shvarev, E. P.; Zvereva, Y. A; Pen'Kov, E. I.; Gladyshev, G. P.; "Acceleration of the polymerization in bulk (suspension) of vinyl chloride at high degrees of conversion"; Vysokomol. Soedin., Ser. A. 17(6), 1226–1228 (Russian) 1975.

*Primary Examiner*—Alan Siegel
(74) *Attorney, Agent, or Firm*—Burns, Daone, Swecker & Mathis, L.L.P.

(57) ABSTRACT

A process is provided for the stabilization of polychlorinated alkanes against dehydrochlorination. The process comprises adding a phenol compound to a polychlorinated alkane such that the dehydrochlorination of the polychlorinated alkane is suppressed when heated in the presence of iron(III). In a preferred embodiment, the process comprises the prevention or reduction of dehydrochlorination of 1,1,1,3,3-pentachloropropane when heated in the presence of iron(III) contamination by the addition of monomethyl ether hydroquinone. In another embodiment, the long term storage stability of polychlorinated alkanes against dehydrochlorination is improved due to the addition of a phenol compound.

48 Claims, No Drawings

DEHYDROCHLORINATION STABILIZATION OF POLYCHLORINATED ALKANES

BACKGROUND OF THE INVENTION

1. Field of the Invention

The present invention relates to a process for the stabilization of polychlorinated alkanes against dehydrochlorination. More particularly, the present invention relates to the prevention or reduction of dehydrochlorination of 1,1,1,3,3-pentachloropropane when heated in the presence of iron (III) contamination by the addition of monomethyl ether hydroquinone.

2. Brief Description of Art

The Montreal Protocol of 1987 placed a ban on certain substances that deplete the ozone layer, especially chlorofluorocarbons (CFC's). To hasten the elimination of CFC production and use, the Protocol allowed for certain fluorocarbon products (HCFC's) to be used as "bridge replacements." Although these bridge replacements are considerably more ozone friendly than CFC's, they are intended to be transitional and not permanent replacements. Fluorocarbon producers are actively pursuing replacement candidates known as "third generation fluorocarbons." These third generation fluorocarbons will require hydrochlorocarbon feedstocks.

The second largest U.S. fluorochemical end-use market, next to refrigeration, is for blowing agents utilized in the manufacture of various synthetic plastic formed products. CFC-11 was the dominant product in this market; however, it has been replaced by the bridge-fluorocarbon HCFC-141b. Because current regulations require foam manufacturers to transition away from HCFC-141b by the year 2003, new third generation fluorocarbon products must be developed and commercialized.

Several fluorochemical producers have targeted fluorocarbon 1,1,1,3,3-pentafluoropropane, utilizing 1,1,1,3,3-pentachloropropane (5CP) as the hydrochlorocarbon feedstock, as the primary replacement product for foam blowing applications. The commercial production of 5CP results in a product which is purified through a series of distillation steps. The presence of iron catalyst used in the reaction to produce 5CP, however, allows for the possibility of iron contamination of the product purification section of such a commercial plant. In addition, many non-ferrous alloys actually contain small amounts of iron which can contribute trace quantities of iron to process streams if any corrosion occurs.

Polychlorinated alkanes such as 1,1,1,3,3-pentachloropropane are known to be susceptible to dehydrochlorination in the presence of iron(III). Since iron is or may be present in the process operation steps downstream from the reactor, a need therefore exists to reduce or prevent dehydrochlorination of 5CP in the presence of iron(III).

Various additives are known to be useful to prevent the oxidation and/or polymerization of halogenated compounds such as polychlorinated alkanes in the presence of air or various metals. One such compound, monomethyl ether hydroquinone, also known as MEHQ or p-methoxyphenol, is well known as an additive for halogenated compounds to prevent oxidation and/or polymerization.

Kita et al (JP Kokai 50088007, "Stabilization of 1,1,1-Trichloro-ethane") and Marsden et al (GB 1265567, "Stabilizers for 1,1,1-Trichloro-ethane"), for example, describe the use of MEHQ to stabilize 1,1,1-trichloroethane against oxidation in the presence of aluminum. Nakatsukasa et al (JP 47011045 B4, "Stabilization of Trichloroethylene or Tetrachloroethylene"), Campbell et al (DE 2008617, "Stabilized Trichloroethylene"), and others, describe the use of MEHQ to stabilize trichloroethylene and/or tetrachloroethylene against heat, light, air, humidity, and contact with metals. Numerous authors also disclose the use of MEHQ to inhibit polymerization of vinyl monomers, including vinyl chloride, vinylidene chloride, or other vinyl group-containing monomers (e.g., JP Kokai 48092310 to Oshima et al, "Vapor-Phase Polymerization inhibition of vinylidene chloride"; DE 2148185 to Fruhwirth et al, "Polymerization inhibitor for vinyl group-containing aliphatic, aromatic, and heterocyclic compounds"; U.S. Pat. No. 3,696,050 to Wert et al, "Polymerization inhibitors for vinyl monomers and unsaturated polyesters"; U.S. Pat. No. 3,346,551 to Moakes, "Stabilization of vinylidene chloride"). However, these documents describe MEHQ as preventing oxidation, hydrolysis, or polymerization; suppression of dehydrochlorination is not mentioned.

Several patents also teach stabilization of fluorinated alkanes with MEHQ. These fluoroalkanes are used in vapor degreasing applications or cleaning of circuit boards. However, MEHQ is used to prevent oxidation, hydrolysis, or polymerization, rather than dehydrochlorination. See, for example, Cook et al (U.S. Pat. No. 4,961,870, "Azeotrope-like compositions of 1,1,2-trichloro-1,2,2-trifluoro-ethane, 1,2-dichlorethylene, and alkanol having 3 to 7 carbon atoms") and Gorski (U.S. Pat. No. 4,804,493, "Stabilized azeotrope or azeotrope-like composition of 1,1,2-trichloro-1,2,2-trifluoroethane and trans-1,2-dichloroethylene for cleaning circuit boards" and U.S. Pat. No. 4,803,009 A, "Stabilized azeotrope or azeotrope-like composition of 1, 1,2-trichloro-1,2,2-trifluoroethane, methanol, and 1,2-dichloroethylene for cleaning circuit boards").

Brooks et al (U.S. Pat. No. 5,683,554, "F141B Crude Stabilization") discloses the addition of various compounds, including MEHQ, to prevent the formation of 1,1-difluoro-1-chloroethane (F142b) when heating 1,1-dichloro-1-fluoroethane (F141b) in a distillation column. In the background disclosure, it is postulated that 142b "results from a breakdown of 141b to 1130 (1,1-dichloroethylene) and HF which, in turn, reacts with 141b to produce 142b." However, suppression of dehydrochlorination is not mentioned, even though these compounds contain chlorine. Instead, only the formation of F142b, not dehydrohalogenation of 141b, is disclosed.

In view of the susceptibility of polychlorinated alkanes such as 1,1,1,3,3-pentafluoropropane (5CP) to dehydrochlorination in the presence of iron(III), a need therefore continues to exist to provide a process which suppresses the dehydrochlorination of such polychlorinated alkanes.

OBJECTS AND SUMMARY OF THE INVENTION

It is an object of the present invention to provide a process which suppresses the dehydrochlorination of polychlorinated alkanes. The process preferably reduces or prevents the dehydrochlorination of polychlorinated alkanes when heated in the presence of iron(III), or the dehydrochlorination of polychlorinated alkanes under storage conditions. More particularly, in a preferred embodiment, the process reduces or prevents the dehydrochlorination of 1,1,1,3,3-pentachloropropane (5CP) when heated in the presence of iron(III). In another preferred embodiment, the process reduces or prevents the dehydrochlorination of 1,1,1,3,3-pentachloropropane (5CP) under storage conditions.

In accordance with one aspect of the present invention, a process is provided which suppresses the dehydrochlorination of a polychlorinated alkane when heated in the presence of iron(III) by adding an effective amount of a phenol compound to suppress dehydrochlorination. A process is also provided which suppresses the dehydrochlorination of a polychlorinated alkane under storage conditions by adding an effective amount of a phenol compound to suppress dehydrochlorination.

In accordance with another aspect of the invention, the process of the invention provides the addition of an effective amount of a phenol compound which is unsubstituted or substituted in one or more ring positions during the production, manufacture or storage of a polychlorinated alkane to suppress dehydrochlorination due to the presence of iron(III) contamination. Crude polychlorinated alkanes are usually prepared in a reaction vessel using a suitable catalyst system. The catalyst is subsequently removed from the crude product. The product is then sent to one or more fractionating columns for purification. At least two columns will typically be utilized for such product purification. Dehydrochlorination of the desired product due to iron(III) contamination may occur in any or all of the columns utilized in such a process. For this reason, dehydrochlorination stabilization may be necessary in any or all of such columns. The dehydrochlorination stabilizer may therefore be added to any or all of such columns as needed to suppress the dehydrochlorination of the polychlorinated alkane. It may also be added to one or more polychlorinated alkanes, or mixtures thereof, in order to improve the storage stability of the polychlorinated alkane(s).

DETAILED DESCRIPTION OF THE PREFERRED EMBODIMENTS OF THE INVENTION

The process of the invention relates to the addition of an effective amount of a phenol compound to suppress dehydrochlorination of polychlorinated alkanes due to the presence of iron(III) contamination.

In an exemplary embodiment, the process of the invention includes the addition of an effective amount of monomethyl ether hydroquinone (MEHQ) during the production, manufacture or storage of 1,1,1,3,3-pentachloropropane to suppress dehydrochlorination due to the presence of iron(III) contamination. The crude 1,1,1,3,3-pentachloropropane will usually be prepared in a reaction vessel using a suitable catalyst system. The catalyst is removed from the crude product, which is then sent to one or more fractionating columns for purification. The column(s) will preferably be operated at subatmospheric pressure. Typically, at least two columns will be used; the first will remove light ends in an overhead fraction while the pentachloropropane product and heavy ends are removed in the bottoms fraction. The bottoms are then sent to a second column in which purified pentachloropropane product is removed overhead and the heavy ends comprise the tower bottoms. Dehydrochlorination of the desired product due to iron(III) contamination can occur in either or any of the columns, although it is more likely to occur in the bottoms of the second or final tower. A dehydrochlorination stabilizer such as MEHQ can be added to any of the columns as needed.

In a preferred embodiment, MEHQ is utilized as the dehydrochlorination stabilizer and is added to the feed to the first tower. In this way, the MEHQ will effectively inhibit dehydrochlorination in the first tower and will also concentrate in the tower bottoms. It will then pass with the unfinished pentachloropropane product in the bottoms fraction into the second and any subsequent columns, where it will continue to suppress dehydrochlorination of the pentachloropropane.

One process for the manufacture of 1,1,1,3,3-pentachloropropane is disclosed in commonly-assigned copending U.S. application Ser. No. 09/671,993 filed Sept. 29, 2000, the di incorporated herein in its entirety. U.S. Pat. No. 5,902,914, herein incorporated by reference, discloses a process for the preparation of halogenated alkanes including 1,1,1,3,3-pentachloropropane, pentachlorobutane, and heptachlorohexane. U.S. Pat. No. 6,187,978, herein incorporated by reference, further discloses a continuous process for preparing halogenated alkanes using an addition reaction.

By the phrase "suppress dehydrochlorination," it is intended that dehydrochlorination of the polychlorinated alkane when heated in the presence of iron(III), or during storage of the polychlorinated alkane, is preferably reduced or prevented.

The degree of suppression of dehydrochlorination of the polychlorinated alkane due to heating in the presence of iron(III), or during storage of the polychlorinated alkane, may be determined by measuring the effect of the dehydrochlorination stabilizer on the rate of formation of dehydrochlorination by-products present in the polychlorinated alkane product. One such suitable method includes a comparison of the rate of formation of one or more of such dehydrochlorination by-products present in the polychlorinated alkane after it is heated or stored in the presence of iron (III) and in the absence of the dehydrochlorination stabilizer with the rate of formation of the same one or more such dehydrochlorination by-products present in the polychlorinated alkane after it is heated or stored in the presence of iron (III) and the dehydrochlorination stabilizer. In general terms, the degree of dehydrochlorination suppression, i.e. the percentage reduction in the rate of formation of such one or more dehydrochlorination by-products, may be determined for such by-products according to formula (I):

$$DDS = \frac{(R_1 - R_2)}{R_1} \times 100 \tag{I}$$

wherein,
DDS=degree of dehydrochlorination suppression, in percent;
$R_1$=average rate of formation of the dehydrochlorination by-product upon heating or storage in the absence of the dehydrochlorination stabilizer (excluding the first overhead sample); and
$R_2$=average rate of formation of the dehydrochlorination by-product upon heating or storage in the presence of the dehydrochlorination stabilizer (excluding the first overhead sample).

The suppression of the dehydrochlorination of a polychlorinated alkane when heated in the presence of iron (III) may be determined using the rate of formation of a dehydrochlorination by-product which appears in the overhead product of one or more distillation columns operating at reflux conditions. In one aspect of the invention, the rate of formation of 1,1,3,3-tetrachloropropene (4CPe) expressed in grams/hr may be determined from the amount of 4CPe in the overhead samples and the total time at reflux conditions. An average rate of formation of 4CPe may then be calculated by measuring the amount of 4CPe collected from the overhead over the period of time during which the samples are collected. Since the first sample may contain 4CPe that was present in the initial charge, and may therefore not accurately represent the amount of 4CPe actually formed during the test, it may be excluded from the calculation of the average rate of formation of 4CPe. By calculating the average rate of formation of a dehydrochlorination by-product such as 4CPe which appears in the overhead when a dehydrochlorination stabilizer such as MEHQ is not added, and the average rate of formation of a dehydrochlorination by-product which appears in the overhead when a dehydrochlorination stabilizer is added, the degree of dehydrochlorination suppression (DDS) according to formula (I) may be calculated.

The determination of the degree of dehydrochlorination suppression by the above-described method is based partly upon the assumption that all the dehydrochlorination by-product is recovered in the overhead. In the case of dehydrochlorination stabilization of 5CP, where the rate of formation of 4CPe may be used to determine the effectiveness of a stabilizer such as MEHQ, a low dehydrochlorination rate should reflect an accurate measurement since virtually all of the 4CPe is expected to be present in the column overhead. Where no stabilizer such as MEHQ is added, and high iron concentrations exist, a dehydrochlorination by-product such as 4CPe may also be present in the column and the bottoms. The determination of the rate of formation of a dehydrochlorination by-product according to the above method under these circumstances may therefore be somewhat understated. The degree of dehydrochlorination suppression (DDS) may be calculated using these "baseline" cases to illustrate the improvement in stabilization due to the added dehydrochlorination stabilizer.

In another embodiment of the invention, a dehydrochlorination stabilizer according to the present invention may be added to one or more polychlorinated alkanes, or mixtures thereof, to improve the storage stability of the polychlorinated alkane(s). Typically, long term storage may include the use of metallic or plastic containers, where water may also be present. Under these conditions, organic decomposition products, including, but not limited to, dehydrochlorination products may be formed. By adding one or more stabilizers according to the present invention, the rate of formation of one or more such decomposition or dehydrochlorination products may be suppressed.

Measurement of the storage stability of polychlorinated alkanes, and of the effects of a dehydrochlorination stabilizer according to the present invention, may be performed by accelerated storage stability testing. One such typical procedure includes the use of small test samples of liquid, typically 50–100 ml, placed in sealed glass or plastic bottles at essentially atmospheric pressure. The vapor space above the samples may be purged, e.g., with either air or nitrogen. Baseline tests to establish a control are conducted with pure solvent (polychlorinated alkane) alone. Metallic or plastic coupons representing the material of construction of the intended storage containers are placed in some of the bottles and either partially or wholly immersed in the liquid. Varying amounts of water may also be added. The bottles are placed in a laboratory oven at approximately 45–55° C. to accelerate any degradation that may occur at the lower ambient temperatures which a solvent may typically encounter during storage. An oven with a lighted interior may also be used if it is desired to investigate the effect of light on solvent decomposition. Analysis of decomposition products may be performed at regular intervals (typically at 7, 14, 30, 60 and 90 days) by removing samples from the laboratory oven. Typical analyses include, but are not limited to, acidity, chloride, water or metals content. Gas chromatography may also be used to determine the presence of decomposition products, including, but not limited to, dehydrochlorination products.

The degree of dehydrochlorination suppression, expressed as a percentage reduction in the average rate of formation of one or more dehydrochlorination by-products produced when a polychlorinated alkane is heated or stored in the presence of a dehydrochlorination stabilizer, is preferably at least about 5% to about 100%, more preferably at least about 20% to about 100%, and especially preferably at least about 50% to about 100%. It is most preferred that the degree of dehydrochlorination stabilization is at least about 90% to about 100%.

The term "effective amount" as used herein is intended to mean that the amount of the dehydrochlorination stabilizer is sufficient to suppress the dehydrochlorination of the polychlorinated alkane. The term "storage conditions" is intended to refer to the conditions under which polychlorinated alkanes and solvents are typically stored. Such conditions usually include ambient temperatures and pressures associated with the storage of chemicals in metallic, plastic or other suitable containers.

Under storage conditions, it is preferred that the degree of dehydrochlorination suppression ranges noted above, expressed as a percentage reduction in the average rate of formation of one or more dehydrochlorination by-products produced when a polychlorinated alkane is stored in the presence of a dehydrochlorination stabilizer, are preferably maintained over a time period of at least about 30 days, more preferably at least about 60 days, and especially preferably at least about 90 days. It is most preferred that the degree of dehydrochlorination stabilization ranges noted above are maintained for at least about 6 months.

In a preferred embodiment, the addition of the phenol compound, preferably MEHQ, to suppress dehydrochlorination of the polychlorinated alkane, preferably 5CP, is added at an effective amount from about 1 to about 120 times the soluble iron concentration in the crude product on a weight basis. An MEHQ/iron weight ratio of from about 5 to about 30 times is more preferred. An MEHQ/iron weight ratio of about 5 to about 10 is especially preferred, and a ratio of about 10 most preferred.

The phenol compound may be unsubstituted or substituted at one or more ring positions. The phenol compound is preferably substituted at one or more ring positions with a substituent selected from hydroxy, alkyl or alkoxy groups, more preferably alkoxy groups. Suitable alkyl groups include lower alkyl groups generally having from 1 to 7 carbon atoms, such as methyl, ethyl, isopropyl, butyl and tert-amyl substituents. For example, p-tert-amyl phenol (PTAP) may be one such suitable alkyl-substituted phenol compound. Suitable alkoxy groups include alkoxy groups generally having from 1 to 7 carbon atoms, such as methoxy, ethoxy, isopropoxy and butoxy substituents. An especially preferred phenol compound is p-methoxyphenol, also known as monomethyl ether hydroquinone or MEHQ.

Although the process has been illustrated herein to reduce or prevent dehydrochlorination in pentachloropropane, it may also be employed to suppress dehydrochlorination in other polychlorinated alkanes. Such polychlorinated alkanes may include those having the general formula $C_xH_yCl_z$, where x can range from 2 to about 15, preferably from about 2 to about 8 and more preferably from about 2 to about 6, y can range from 1 to about (2x+1) and z can range from 1 to about (2x+1). Such polychlorinated alkanes may include, but are not limited to, 1,1,1-trichloroethane, 1,1,2-trichloroethane, 1,1,1,2,3-pentachloropropane, 1,1,1,3,3-pentachlorobutane, 1,1,1,3-tetrachloropropane, hexachloropropanes, such as 1,1,1,3,3,3-hexachloropropane, 1,1,1,3,3,5-hexachloropentane (or an isomer thereof) and 1,1,1,3,3,5,5,5-octachloropentane (or an isomer thereof).

EXAMPLES

Tests were conducted by refluxing various mixtures in a laboratory 10-tray, one-inch Pyrex Oldershaw distillation column operated at about 320 and 410 torr. These pressures were chosen so that the bottoms temperature would be approximately 155 and 165 degrees C. (310 and 330 degrees F.), respectively. The one-liter bottoms flask was charged with about 500 grams of the desired test solution. Normally, the column was operated on total reflux. Periodically, the reflux timer was activated so as to give a 4/1 reflux ratio, and small overhead samples (15 to 25 grams) were drawn. The samples were analyzed by gas chromatograph for tetrachloropropene content, and the vapor space over the samples was qualitatively checked for acidity using pH paper. Along with the overhead temperature, both of these parameters were used as indicators of 5CP dehydrochlorination in the bottoms.

Starting solutions were prepared using either crude or purified pentachloropropane. The desired amount of either ferric chloride or hydrated ferric oxide, FeO(OH), was weighed into the dry bottoms flask already attached to the distillation column. MEHQ was then weighed into the flask, if appropriate to the test, 5CP was added, and the solution stirred for a few minutes at room temperature with a Teflon-coated magnetic spin bar. Vacuum and heat were applied, and the system was allowed to come to reflux.

The origin and composition of the test reagents are shown below:

| Component, wt % | Purified pentachloropropane | Crude Pentachloropropane |
|---|---|---|
| Light Ends (b.p. < 5 CP) | 0.100 | 0.077 |
| Tetrachloropropene | 0.009 | 0.003 |
| 5 CP | 99.883 | 99.126 |
| HCC-240 db (5 CP isomer) | 0.006 | 0.371 |
| Heavy Ends (b.p. > isomer) | 0.002 | 0.423 |
| ppm Fe | n/a | 1 |

Example 1

In Example 1, crude pentachloropropane alone was refluxed with no iron or MEHQ added. About 1 ppm Fe was present in the sample as received. The bottoms temperature was initially 157° C. Slight dehydrochlorination was observed, evidenced by the appearance of 1,1,3,3-tetrachloropropene (4CPe) in the overhead at quantities larger than expected by concentration alone. This is shown in Table I by comparing the weight of 4CPe in each overhead sample to the total amount in the initial charge. The 4CPe in the overhead dropped from 0.14 grams in the first sample to 0.04 grams in the second (samples 1 and 2, respectively), indicating that 4CPe was forming more slowly than it was being removed overhead. The temperature was raised to 165° C. and the solution allowed to reflux for almost another hour before the final two samples were taken. The first sample 3 again contained about 0.14 grams of 4CPe; and the second contained 0.09 grams, indicating that the dehydrochlorination rate was somewhat higher than in the lower temperature tests. Also, a small amount of acidity was present in the vapor associated with the last two overhead samples. As shown in Table II, the average rate of formation of 4CPe was 0.19 g/hr, excluding the first overhead sample. Example 1 is used as a baseline case to illustrate the improvement in stabilization using MEHQ in Example 2.

TABLE I

MEHQ as Dehydrochlorination Stabilizer for Iron(III)-Containing 1,1,1,3,3-Pentachloropropane

| | Example 1 | | | | Example 2 | | | | Example 3 | | Example 4 | | |
|---|---|---|---|---|---|---|---|---|---|---|---|---|---|
| Initial Charge: | | | | | | | | | | | | | |
| grams Purified 5CP | — | | | | — | | | | — | | 462.2 | | |
| grams Crude 5CP | 503.2 | | | | 492.4 | | | | 546.53 | | — | | |
| ppm MEHQ | 0 | | | | 113 | | | | 0 | | 119 | | |
| ppm Fe(III) | 1 | | | | 1 | | | | 17 | | 12 | | |
| Fe added as: | None added | | | | None added | | | | FeCl$_3$ | | FeCl$_3$ | | |
| MEHQ/Fe (wt.) | 0 | | | | 113 | | | | 0 | | 10 | | |
| Overhead Sample: | | | | | | | | | | | | | |
| Sample Number | 1 | 2 | 3 | 4 | 5 | 6 | 7 | 8 | 9 | 10 | 11 | 12 | 13 |
| Amount, grams | 19.1 | 29 | 17.9 | 22.4 | 17.9 | 21.8 | 18 | 22.4 | 9.3 | 9.1 | 17.8 | 18.8 | 19.1 |
| Composition, wt %: | | | | | | | | | | | | | |
| Light Ends | 0.294 | 0.091 | 0.115 | 0.083 | 0.294 | 0.116 | 0.093 | 0.068 | 1.112 | 1.132 | 0.115 | 0.077 | 0.056 |
| HCC-1230za (4CPe) | 0.721 | 0.135 | 0.799 | 0.422 | 0.309 | 0.035 | 0.037 | 0.008 | 74.380 | 74.298 | 1.103 | 0.324 | 0.063 |
| HCC-240fa (5CP) | 98.919 | 99.693 | 99.018 | 99.406 | 99.339 | 99.770 | 99.778 | 99.828 | 24.495 | 24.551 | 98.782 | 99.599 | 99.881 |
| HCC-240db (5CP isomer) | 0.066 | 0.081 | 0.068 | 0.090 | 0.058 | 0.070 | 0.092 | 0.097 | 0.017 | 0.018 | | | |
| HCl in sample vapor? | No | No | Slight | Slight | No | No | No | No | Yes | Yes | No | No | No |
| Overhead Temp., ° C. | 153–154 | 154 | 161 | 161–162 | 153 | 153 | 162 | 162 | 120–123 | 123–125 | 151–152 | 152 | 152 |
| Vacuum, in. Hg | 15.8 | 15.8 | 12.5 | 12.5 | 15.8 | 15.8 | 12.5 | 12.5 | 15.8 | 15.8 | 15.7 | 15.8 | 15.8 |

TABLE I-continued

MEHQ as Dehydrochlorination Stabilizer for Iron(III)-Containing 1,1,1,3,3-Pentachloropropane

| Bottoms Temp, °C: | 157 | 157 | 165 | 165 | 157 | 157 | 165 | 165 | 151 | 151 | 157 | 157 | 157 |
|---|---|---|---|---|---|---|---|---|---|---|---|---|---|
| Total Time at Reflux (hours) | 0.87 | 1.08 | 2.02 | 2.32 | 0.53 | 0.70 | 1.18 | 1.37 | 0.30 | 1.38 | 0.82 | 1.27 | 1.42 |
| Grams HCC-1230za (4CPe): | | | | | | | | | | | | | |
| In Initial Charge | 0.02 | 0.02 | 0.02 | 0.02 | 0.02 | 0.02 | 0.02 | 0.02 | 0.02 | 0.02 | 0.04 | 0.04 | 0.04 |
| In Overhead Sample | 0.14 | 0.04 | 0.14 | 0.09 | 0.06 | 0.01 | 0.01 | 0.00 | 6.92 | 6.76 | 0.20 | 0.06 | 0.01 |

| | Example 5 | | | | Example 6 | | | | Example 7 | | Example 8 | |
|---|---|---|---|---|---|---|---|---|---|---|---|---|
| Initial Charge: | | | | | | | | | | | | |
| grams Purified 5CP | 496.3 | | | | 404.1 | | | | 458.4 | | 376.6 | |
| grams Crude 5CP | — | | | | — | | | | — | | — | |
| ppm MEHQ | 946 | | | | 2275 | | | | 0 | | 2435 | |
| ppm Fe(III) | 187 | | | | 230 | | | | 206 | | 250 | |
| Fe added as: | FeCl$_3$ | | | | FeCl$_3$ | | | | FeO(OH) | | FeO(OH) | |
| MEHQ/Fe (weight) | 5 | | | | 10 | | | | 0 | | 10 | |
| Overhead Sample: | | | | | | | | | | | | |
| Sample Number | 14 | 15 | 16 | 17 | 18 | 19 | 20 | 21 | 22 | 23 | 24 | 25 |
| Amount, grams | 22.4 | 19 | 26 | 24.8 | 19.9 | 30.7 | 15 | 14.1 | 19 | 27.7 | 20.4 | 23.1 |
| Composition, wt %: | | | | | | | | | | | | |
| Light Ends | 0.461 | 0.250 | 0.189 | 0.214 | 0.205 | 0.120 | 0.126 | 0.168 | 0.979 | 0.139 | 0.123 | 0.117 |
| HCC-1230za (4-CPe) | 4.417 | 0.582 | 0.335 | 0.606 | 0.685 | 0.108 | 0.103 | 0.158 | 96.467 | 1.101 | 0.170 | 0.196 |
| HCC-240fa (5CP) | 95.094 | 99.166 | 99.476 | 99.180 | 99.111 | 99.772 | 99.771 | 99.674 | 2.554 | 98.760 | 99.706 | 99.688 |
| HCC-240db (5CP isomer) | | | | | | | | | | | | |
| HCl in sample vapor? | No | Slight | Slight | Slight | No | No | Slight | Slight | Yes | No | No | No |
| Overhead Temp., °C. | 147–151 | 151 | 151 | 150–151 | 148–150 | 150 | 150 | 150 | 120 | 150 | 150 | 150 |
| Vacuum, in. Hg | 16.0 | 16.0 | 15.9 | 16.0 | 16.1 | 16.0 | 16.0 | 16.0 | 16.0 | 16.0 | 16.0 | 16.0 |
| Bottoms Temp., °C. | 155 | 155 | 155 | 155 | 155 | 155 | 155 | 155 | 127 | 155 | 155 | 155 |
| Total Time at Reflux (hours) | 0.77 | 0.95 | 1.15 | 2.52 | 0.42 | 0.75 | 1.02 | 2.03 | 7.75 | 0.87 | 1.02 | 1.87 |
| Grams HCC-1230za (4CPe): | | | | | | | | | | | | |
| In Initial Charge | 0.04 | 0.04 | 0.04 | 0.04 | 0.03 | 0.03 | 0.03 | 0.03 | 0.04 | 0.03 | 0.03 | 0.03 |
| In Overhead Sample | 0.99 | 0.11 | 0.09 | 0.15 | 0.14 | 0.03 | 0.02 | 0.02 | 18.33 | 0.30 | 0.03 | 0.05 |

TABLE II

Degree of Dehydrochlorination Suppression Using MEHQ for Iron(III)-Containing 1,1,1,3,3-Pentachloropropane

| | Example 1 | Example 2 | Example 3 | Example 4 |
|---|---|---|---|---|
| Average 4CPe formation rate (g/hr)[1] | 0.19 | 0.02 | 6.24 | 0.12 |
| Calculated DDS[2] | — | 90 | — | 98 |
| Comparison Example No. | — | 1 | — | 3 |

| | Example 5 | Example 6 | Example 7 | Example 8 |
|---|---|---|---|---|
| Average 4CPe formation rate (g/hr)[1] | 0.20 | 0.04 | 2.37 | 0.08 |
| Calculated DDS[2] | 97 | 99 | — | 97 |
| Comparison Example No. | 3 | 3 | — | 7 |

[1]excluding the first overhead sample.
[2]calculated degree of dehydrochlorination suppression (DDS) according to formula (I).

Example 2

The conditions of Example 1 were repeated using fresh reagents with the addition of 113 ppm MEHQ to the starting solution. The amounts of 4CPe in the first and second overhead samples at 157° C. bottoms temperature were 0.06 and 0.01 grams, respectively. In addition, raising the temperature to 165° C. resulted in essentially no increase in the overhead 4CPe content, indicating that the dehydrochlorination of 5CP had been practically prevented. As shown in Table II, the average rate of formation of 4CPe was 0.02 g/hr, excluding the first overhead sample. The average Degree of Dehydrochlorination Suppression (DDS) relative to Example 1 was 90 percent (calculated according to formula and shown in Table II).

Example 3

In Example 3, fresh crude pentachloropropane was spiked with 17 ppm of iron(III) in the form of FeCl$_3$. Severe dehydrochlorination occurred upon refluxing at the same pressure as before. Overhead fraction sample numbers 9 and 10 were nearly 75 percent 4CPe, and HCl was readily evident in the vapor over the samples. Over 13.5 grams of 4CPe were collected in these two samples. Overhead and bottoms temperatures were also lower, reflecting the higher 4CPe content. This illustrates that even low concentrations of iron(III) are sufficient to catalyze rapid dehydrochlorination of 5CP at these temperatures. As shown in Table II, the average rate of formation of 4CPe was 6.24 g/hr, excluding the first overhead sample. Example 3 is used as a baseline case to illustrate the improvement in stabilization using MEHQ in Examples 4 to 6.

Example 4

Example 4 shows that the addition of 119 ppm MEHQ to T-15 overhead spiked with 12 ppm Fe(III) (again added as FeCl$_3$) effectively suppressed the dehydrochlorination reaction of 5CP. Overhead sample numbers 11 to 13 showed only a small accumulation of 4CPe in the overhead above what was originally charged. Additionally, 4CPe content dropped rapidly from sample to sample, and no HCl was detected in the vapor spaces. As shown in Table II, the average rate of formation of 4CPe was 0.12 g/hr, excluding the first overhead sample. The average Degree of Dehydrochlorination Suppression (DDS) relative to Example 3 was 98 percent (calculated according to formula (I) and shown in Table II).

Example 5

Example 5 shows the effect of MEHQ addition with higher iron concentrations and lower MEHQ/iron ratios. The purified pentachloropropane was spiked with ferric chloride to give 187 ppm iron(III), and 946 ppm MEHQ was added to give an MEHQ/iron weight ratio of 5. Upon refluxing, dehydrochlorination was still greatly suppressed compared to Example 3 with no MEHQ present. However, a slow dehydrochlorination rate was still observed as evidenced by the slight acidity in the overhead vapor samples as well as the slightly elevated levels of 4CPe in comparison with Examples 2 and 4. As shown in Table II, the average rate of formation of 4CPe was 0.20 g/hr, excluding the first overhead sample. The average Degree of Dehydrochlorination Suppression (DDS) relative to Example 3 was 97 percent (calculated according to formula (I) and shown in Table II).

Example 6

The conditions of Example 5 were repeated with 230 ppm iron(III), but with the addition of 2275 ppm MEHQ. This gave a 10/1 weight ratio of MEHQ/iron. Dehydrochlorination was reduced to levels below those of Example 5, as evidenced by the lower concentrations of 4CPe in the overhead samples. As shown in Table II, the average rate of formation of 4CPe was 0.04 g/hr, excluding the first overhead sample. The average Degree of Dehydrochlorination Suppression (DDS) relative to Example 3 was 99 percent (calculated according to formula (I) and shown in Table II).

Example 7

In Example 7, purified pentachloropropane was spiked with 205 ppm iron(III) added as FeO(OH) and refluxed as before. Severe dehydrochlorination occurred, giving an overhead fraction composed of over 96 percent 4CPe. This illustrates that other forms of iron(III) besides FeCl$_3$ are active dehydrochlorination agents. As shown in Table II, the average rate of formation of 4CPe was 2.37 g/hr, excluding the first overhead sample. Example 7 is used as a baseline case to illustrate the improvement in stabilization using MEHQ in Example 8.

Example 8

The conditions of Example 7 were repeated with 205 ppm iron(III) added as FeO(OH), but with the addition of 2435 ppm MEHQ. Dehydrochlorination on refluxing was almost entirely eliminated, as evidenced by the lack of HCl and small amounts of 4CPe in the overhead samples. As shown in Table II, the average rate of formation of 4CPe was 0.08 g/hr, excluding the first overhead sample. The average Degree of Dehydrochlorination Suppression (DDS) relative to Example 7 was 97 percent (calculated according to formula (I) and shown in Table II).

While the invention has been described in detail by reference to specific embodiments, the skilled artisan will appreciate that various modifications, substitutions, omissions and changes may be made, and equivalents employed, without departing from the spirit of the invention or the scope of the appended claims.

What is claimed is:

1. A process for stabilizing a polychlorinated alkane from dehydrochlorination in the presence of iron(III) which comprises, adding an effective amount of a phenol compound which is unsubstituted or substituted at one or more ring positions, to suppress the dehydrochlorination of the polychlorinated alkane when heated in the presence of iron(III).

2. The process of claim 1, wherein the polychlorinated alkane is selected from polychlorinated alkanes having the general formula $C_xH_ycl_z$, wherein x is from 2 to about 15, y is from 1 to about (2x+1) and z is from 1 to about (2x+1).

3. The process of claim 2, wherein x is from about 2 to about 8.

4. The process of claim 2, wherein x is from about 2 to about 6.

5. The process of claim 1, wherein the polychlorinated alkane is selected from pentachloropropane or hexachloropropane.

6. The process of claim 1, wherein the polychlorinated alkane is selected from 1,1,1-trichloroethane, 1,1,2-trichloroethane, 1,1,1,2,3-pentachloropropane, 1,1,1,3,3-pentachlorobutane, 1,1,1,3-tetrachloropropane, 1,1,1,3,3,3-hexachloropropane, 1,1,1,3,3,5-hexachloropentane or an isomer thereof or 1,1,1,3,3,5,5,5-octachloropentane or an isomer thereof.

7. The process of claim 1, wherein the phenol compound is substituted at one or more ring positions with a substituent selected from hydroxy, alkyl or alkoxy groups.

8. The process of claim 7, wherein the phenol compound is an alkoxy substituted phenol.

9. The process of claim 8, wherein the alkoxy substituted phenol is p-methoxyphenol.

10. The process of claim 1, wherein the effective amount of the phenol compound is from about 1 to about 120 times the soluble iron concentration on a weight basis.

11. The process of claim 1, wherein the effective amount of the phenol compound is from about 5 to about 30 times the soluble iron concentration on a weight basis.

12. The process of claim 1, wherein the effective amount of the phenol compound is about 10 times the soluble iron concentration on a weight basis.

13. The process of claim 1, wherein the degree of dehydrochlorination suppression is at least about 5% to about 100%.

14. The process of claim 1, wherein the degree of dehydrochlorination suppression is at least about 20% to about 100%.

15. The process of claim 1, wherein the degree of dehydrochlorination suppression is at least about 50% to about 100%.

16. The process of claim 1, wherein the degree of dehydrochlorination suppression is at least about 90% to about 100%.

17. A process for stabilizing 1,1,1,3,3-pentachloropropane from dehydrochlorination in the presence of iron(III) which comprises, adding an effective amount of monomethyl ether hydroquinone to suppress the dehydrochlorination of the 1,1,1,3,3-pentachloropropane when heated in the presence of iron(III).

18. The process of claim 17, wherein the effective amount of the monomethyl ether hydroquinone is from about 1 to about 120 times the soluble iron concentration on a weight basis.

19. The process of claim 17, wherein the effective amount of the monomethyl ether hydroquinone is from about 5 to about 30 times the soluble iron concentration on a weight basis.

20. The process of claim 17, wherein the effective amount of the monomethyl ether hydroquinone is about 10 times the soluble iron concentration on a weight basis.

21. The process of claim 17, wherein the degree of dehydrochlorination suppression is at least about 5% to about 100%.

22. The process of claim 17, wherein the degree of dehydrochlorination suppression is at least about 20% to about 100%.

23. The process of claim 17, wherein the degree of dehydrochlorination suppression is at least about 50% to about 100%.

24. The process of claim 17, wherein the degree of dehydrochlorination suppression is at least about 90% to about 100%.

25. A process for stabilizing a polychlorinated alkane under storage conditions from dehydrochlorination in the presence of iron(III) which comprises, adding an effective amount of a phenol compound which is unsubstituted or substituted at one or more ring positions, to suppress the dehydrochlorination of the polychlorinated alkane.

26. The process of claim 25, wherein the polychlorinated alkane is selected from polychlorinated alkanes having the general formula $C_xH_yCl_z$, wherein x is from 2 to about 15, y is from 1 to about (2x+1) and z is from 1 to about (2x+1).

27. The process of claim 26, wherein x is from about 2 to about 8.

28. The process of claim 26, wherein x is from about 2 to about 6.

29. The process of claim 25, wherein the polychlorinated alkane is selected from pentachloropropane or hexachloropropane.

30. The process of claim 25, wherein the polychlorinated alkane is selected from 1,1,1-trichloroethane, 1,1,2-trichloroethane, 1,1,1,2,3-pentachloropropane, 1,1,1,3,3-pentachlorobutane, 1,1,1,3-tetrachloropropane, 1,1,1,3,3,3-hexachloropropane, 1,1,3,3,5-hexachloropentane or an isomer thereof or 1,1,1,3,3,5,5,5-octachloropentane or an isomer thereof.

31. The process of claim 25, wherein the phenol compound is substituted at one or more ring positions with a substituent selected from hydroxy, alkyl or alkoxy groups.

32. The process of claim 31, wherein the phenol compound is an alkoxy substituted phenol.

33. The process of claim 32, wherein the alkoxy substituted phenol is p-methoxyphenol.

34. The process of claim 25, wherein the effective amount of the phenol compound is from about 1 to about 120 times the soluble iron concentration on a weight basis.

35. The process of claim 25, wherein the effective amount of the phenol compound is from about 5 to about 30 times the soluble iron concentration on a weight basis.

36. The process of claim 25, wherein the effective amount of the phenol compound is about 10 times the soluble iron concentration on a weight basis.

37. The process of claim 25, wherein the degree of dehydrochlorination suppression is at least about 5% to about 100% over a time period of at least about 6 months.

38. The process of claim 25, wherein the degree of dehydrochlorination suppression is at least about 20% to about 100% over a time period of at least about 6 months.

39. The process of claim 25, wherein the degree of dehydrochlorination suppression is at least about 50% to about 100% over a time period of at least about 6 months.

40. The process of claim 25, wherein the degree of dehydrochlorination suppression is at least about 90% to about 100% over a time period of at least about 6 months.

41. A process for stabilizing 1,1,1,3,3-pentachloropropane under storage conditions from dehydrochlorination in the presence of iron(III) which comprises, adding an effective amount of monomethyl ether hydroquinone to suppress the dehydrochlorination of the 1,1,1,3,3-pentachloropropane.

42. The process of claim 41, wherein the effective amount of the monomethyl ether hydroquinone is from about 1 to about 120 times the soluble iron concentration on a weight basis.

43. The process of claim 41, wherein the effective amount of the monomethyl ether hydroquinone is from about 5 to about 30 times the soluble iron concentration on a weight basis.

44. The process of claim 41, wherein the effective amount of the monomethyl ether hydroquinone is about 10 times the soluble iron concentration on a weight basis.

45. The process of claim 41, wherein the degree of dehydrochlorination suppression is at least about 5% to about 100% over a time period of at least about 6 months.

46. The process of claim 41, wherein the degree of dehydrochlorination suppression is at least about 20% to about 100% over a time period of at least about 6 months.

47. The process of claim 41, wherein the degree of dehydrochlorination suppression is at least about 50% to about 100% over a time period of at least about 6 months.

48. The process of claim 41, wherein the degree of dehydrochlorination suppression is at least about 90% to about 100% over a time period of at least about 6 months.

* * * * *